(12) United States Patent
Syrjä et al.

(10) Patent No.: US 11,351,075 B2
(45) Date of Patent: Jun. 7, 2022

(54) CONFIGURABLE PATIENT SUPPORT FOR ULTRASOUND THERAPY

(71) Applicant: Profound Medical Inc., Mississauga (CA)

(72) Inventors: Antti Matias Syrjä, Vantaa (FI); Aaro Tuominen, Espoo (FI); Raimund Christopher Wieland Jung, Aachen (DE)

(73) Assignee: Profound Medical Inc., Mississauga (CA)

( * ) Notice: Subject to any disclaimer, the term of this patent is extended or adjusted under 35 U.S.C. 154(b) by 154 days.

(21) Appl. No.: 16/937,960

(22) Filed: Jul. 24, 2020

(65) Prior Publication Data

US 2022/0023123 A1   Jan. 27, 2022

(51) Int. Cl.
*A61G 7/05* (2006.01)
*A61G 7/057* (2006.01)
*A61G 99/00* (2006.01)
*G01R 33/48* (2006.01)

(52) U.S. Cl.
CPC ....... *A61G 7/05738* (2013.01); *A61G 7/0528* (2016.11); *A61G 99/00* (2013.01); *G01R 33/4814* (2013.01)

(58) Field of Classification Search
CPC .... A61G 7/05; A61G 7/05738; A61G 7/0528; A61G 13/00; A61G 99/00; G01R 33/4814; A61N 7/02
See application file for complete search history.

(56) References Cited

U.S. PATENT DOCUMENTS

| | | | |
|---|---|---|---|
| 2009/0093708 A1* | 4/2009 | Wang | A61N 7/02 601/2 |
| 2016/0089551 A1* | 3/2016 | Ylihautala | A61N 7/02 601/3 |
| 2017/0001044 A1 | 1/2017 | Mahon et al. | |
| 2018/0085023 A1* | 3/2018 | Tillander | G01R 33/4804 |

FOREIGN PATENT DOCUMENTS

JP   2007275458 A   10/2007

OTHER PUBLICATIONS

ISA, "International Search Report", PCT/IB20/00646, dated Apr. 16, 2021.

* cited by examiner

*Primary Examiner* — Fredrick C Conley (74) *Attorney, Agent, or Firm* — Intrinsic Law Corp.

(57) ABSTRACT

A convertible patient support apparatus includes a patient support bed and a removable patient contact disposed in a hole in the patient support bed. The hole is defined by a support frame. A static membrane is attached to the support frame. One of a plurality of removable patient contacts can be removably attached to the support frame to convert the convertible patient support apparatus based on the patient and/or therapy.

41 Claims, 9 Drawing Sheets

CONFIGURABLE PATIENT SUPPORT FOR ULTRASOUND THERAPY

TECHNICAL FIELD

This application relates generally to patient support systems for MRI-guided ultrasound-therapy treatment.

BACKGROUND

Ultrasonic transducers have been employed in ultrasound therapy systems to achieve therapeutic heating of diseased and other tissues. Arrays of ultrasound transducers operating to form a beam of ultrasonic energy cause a conversion of sound to thermal energy in the affected tissue areas or treatment volumes, and a subsequent beneficial rise in the temperature in the treatment volumes.

In image-guided ultrasound therapy systems, a patient and the ultrasound therapy apparatus, including an ultrasound positioning apparatus, are generally disposed in an imaging volume such as a magnetic resonance imaging (MRI) apparatus, which allows guidance of the applicator placement, and in addition allows monitoring of the treatment effect on the tissue by providing real-time data from which temperature maps can be calculated. A clinical operator can then monitor the progress of the therapy within the treatment volume or diseased tissue and manual or automated changes can be made to the ultrasound power signals based on input from the results and progress of the treatment. With proper monitoring of the heating effect, ultrasound therapy systems can be used to treat harmful cells and to controllably destroy tumors while minimizing damage to healthy tissue.

SUMMARY

Example embodiments described herein have innovative features, no single one of which is indispensable or solely responsible for their desirable attributes. The following description and drawings set forth certain illustrative implementations of the disclosure in detail, which are indicative of several exemplary ways in which the various principles of the disclosure may be carried out. The illustrative examples, however, are not exhaustive of the many possible embodiments of the disclosure. Without limiting the scope of the claims, some of the advantageous features will now be summarized. Other objects, advantages and novel features of the disclosure will be set forth in the following detailed description of the disclosure when considered in conjunction with the drawings, which are intended to illustrate, not limit, the invention.

An aspect of the invention is directed to a convertible patient support apparatus comprising a patient support bed having a hole defined therein; a support frame disposed on or in the hole, the support frame attached to the patient support bed; and a static membrane fixedly attached to the support frame. The convertible patient support apparatus further comprises a removable patient contact including: an interface frame removably attached to the support frame; a patient contact frame fixedly attached to the interface frame; and a patient contact membrane fixedly attached to the interface frame. The patient contact membrane, the static membrane, and the interface frame define a cavity, the cavity having a port to introduce or remove an ultrasound coupling and cooling fluid to or from the cavity.

In one or more embodiments, the static membrane is disposed below the removable patient contact. In one or more embodiments, the static membrane is rigid. In one or more embodiments, the patient contact membrane is deformable.

In one or more embodiments, the port comprises an inlet port, an internal fluid circulation channel is formed between the patient contact frame, the static membrane, and the support frame, and the internal fluid circulation channel provides the ultrasound coupling and cooling fluid to the cavity through the inlet port and receives the ultrasound coupling and cooling fluid from the cavity through the outlet port. In one or more embodiments, the apparatus further comprises an ultrasound coupling and cooling fluid recirculation system; an outlet channel that fluidly couples the outlet port to an input of the ultrasound coupling and cooling fluid recirculation system; and an input channel that fluidly couples an output of the ultrasound coupling and cooling fluid recirculation system to the internal fluid circulation channel. In one or more embodiments, the ultrasound coupling and cooling fluid recirculation system comprises a tank, a pump, a fluid chiller, and a degasser.

In one or more embodiments, the apparatus further comprises mechanical locks that releasably securely attach the interface frame to the support frame.

Another aspect of the invention is directed to a convertible patient support apparatus comprising a patient support bed having a hole defined therein; a support frame disposed on or in the hole, the support frame attached to the patient support bed; and a static membrane fixedly attached to the support frame. The apparatus further comprises a removable patient contact comprising: an interface frame removably attached to the support frame; a patient contact frame fixedly attached to the interface frame; a patient contact membrane fixedly attached to the interface frame; a raised rigid patient contact attached to the patient contact frame, the raised rigid patient contact disposed between the patient contact membrane and the static membrane; and a plurality of circulation channels disposed on or in the raised rigid patient contact. An internal fluid circulation channel is formed between the patient contact frame, the static membrane, and the support frame. The circulation channels are fluidly coupled to one or more inlet ports in the internal fluid circulation channel to receive the ultrasound coupling and cooling fluid. In addition, the circulation channels are fluidly coupled to one or more outlet ports in the internal fluid circulation channel to output the ultrasound coupling and cooling fluid.

In one or more embodiments, the raised rigid patient contact is configured to engage an anatomical structure of a patient during an ultrasound therapeutic treatment when the patient is on the patient support bed. In one or more embodiments, the circulation channels extend parallel to each other.

In one or more embodiments, the circulation channels form a spiral. In one or more embodiments, an output channel is formed through the spiral to receive the ultrasound coupling and cooling fluid from a termination of the circulation channels. In one or more embodiments, the output channel is fluidly coupled to the one or more outlet ports in the internal fluid circulation channel. In one or more embodiments, the output channel is fluidly coupled to an ultrasound coupling and cooling fluid recirculation system. In one or more embodiments, the ultrasound coupling and cooling fluid recirculation system comprises a tank, a pump, a fluid chiller, and a degasser.

In one or more embodiments, the apparatus further comprises mechanical locks that releasably securely attach the interface frame to the support frame.

Yet another aspect of the invention is directed to a kit comprising a convertible patient apparatus and a plurality of removable patient contacts. The convertible patient apparatus comprises a patient support bed having a hole defined therein; a support frame disposed on or in the hole, the support frame attached to the patient support bed; and a static membrane fixedly attached to the support frame. Each removable patient contact includes an interface frame configured to be removably attached to the support frame; a patient contact frame fixedly attached to the interface frame; and a patient contact membrane fixedly attached to the patient contact frame. When the interface frame of one of the removable patient contacts is attached to the support frame to form an attached patient contact, an internal fluid circulation channel is formed between the patient contact frame of the attached patient contact, the static membrane, and the support frame.

In one or more embodiments, the plurality of removable patient contacts includes a first removable patient contact, and when the first removable patient contact is attached to the support frame, the patient contact membrane and the static membrane define a cavity having a port that is fluidly coupled to the internal fluid circulation channel to introduce or remove an ultrasound coupling and cooling fluid to or from the cavity. In one or more embodiments, when the first removable patient contact is attached to the support frame: the port comprises an inlet port, the cavity has an outlet port that is fluidly coupled to the internal fluid circulation channel, and the cavity receives the ultrasound coupling and cooling fluid from the inlet port and outputs the ultrasound coupling and cooling fluid through the outlet port. In one or more embodiments, the internal fluid circulation channel is fluidly coupled to an ultrasound coupling and cooling fluid recirculation system. In one or more embodiments, the ultrasound coupling and cooling fluid recirculation system comprises a tank, a pump, a fluid chiller, and a degasser.

In one or more embodiments, when the first removable patient contact is attached to the support frame, the static membrane is disposed below the first removable patient contact. In one or more embodiments, the patient contact membrane of the first removable patient contact is deformable.

In one or more embodiments, the plurality of removable patient contacts includes a second removable patient contact. In the second removable patient contact: a raised rigid patient contact is attached to the patient contact frame; a plurality of circulation channels are disposed on or in the raised rigid patient contact, the circulation channels configured to receive the ultrasound coupling and cooling fluid from one or more inlet ports in the internal fluid circulation channel to output the ultrasound coupling and cooling fluid to one or more outlet ports in the internal fluid circulation channel; and when the second removable patient contact is attached to the support frame, the raised rigid patient contact of the second removable patient contact is disposed between the patient contact membrane and the static membrane.

In one or more embodiments, the raised rigid patient contact is configured to engage an anatomical structure of a patient during an ultrasound therapeutic treatment when the patient is on the patient support bed, and the second removable patient contact is attached to the support frame. In one or more embodiments, the circulation channels, disposed on or in the raised rigid patient contact, extend parallel to each other. In one or more embodiments, the circulation channels, disposed on or in the raised rigid patient contact, form a spiral. In one or more embodiments, an output channel is formed through the spiral to receive the ultrasound coupling and cooling fluid from a termination of the circulation channels.

In one or more embodiments, the output channel is fluidly coupled to the one or more outlet ports in the internal fluid circulation channel. In one or more embodiments, the output channel is fluidly coupled to an ultrasound coupling and cooling fluid recirculation system. In one or more embodiments, the ultrasound coupling and cooling fluid recirculation system comprises a tank, a pump, a fluid chiller, and a degasser.

In one or more embodiments, the plurality of removable patient contacts includes a third removable patient contact. In the third removable patient contact: the patient contact membrane is rigid; the patient contact membrane, the static membrane, and the interface frame define a cavity having an inlet port and an outlet port that are fluidly coupled to the internal fluid circulation channel; and the cavity receives the ultrasound coupling and cooling fluid from the inlet port in the circulation frame and outputs the ultrasound coupling and cooling fluid through the outlet port.

In one or more embodiments, the kit further comprises mechanical locks that releasably securely attach the interface frame of each removable patient contact to the support frame. In one or more embodiments, the static membrane is rigid.

Another aspect of the invention is directed to a system comprising a convertible patient support and a high intensity focused ultrasound (HIFU) system for sonicating a sonication volume of a patient. The convertible patient support comprises: a patient support bed having a hole defined therein; a support frame disposed on or in the hole, the support frame attached to the patient support bed; a static membrane fixedly attached to the support frame; and a removable patient contact. The removable patient contact comprises: an interface frame removably attached to the support frame; a patient contact frame fixedly attached to the interface frame; and a patient contact membrane fixedly attached to the interface frame. The patient contact membrane, the static membrane, and the interface frame define a cavity, the cavity having a port to introduce or remove an ultrasound coupling and cooling fluid to or from the cavity. The HIFU system includes an ultrasound applicator disposed below the hole in the patient support bed, the ultrasound applicator generating ultrasound energy having a path through the static membrane, the ultrasound coupling and cooling fluid, and the patient contact membrane to reach a target volume in the patient.

In one or more embodiments, the path of the ultrasound energy does not include any structures that are opaque to ultrasound energy transmission.

In one or more embodiments, the port comprises an inlet port, an internal fluid circulation channel is formed between the patient contact frame, the static membrane, and the support frame, and the internal fluid circulation channel provides the ultrasound coupling and cooling fluid to the cavity through the inlet port and receives the ultrasound coupling and cooling fluid from the cavity through the outlet port.

In one or more embodiments, an internal fluid circulation channel is formed between the patient contact frame, the static membrane, and the support frame, the internal fluid circulation channel providing the ultrasound coupling and cooling fluid to the cavity through the inlet port and receiving the ultrasound coupling and cooling fluid from the cavity through the outlet port.

In one or more embodiments, the system further comprises: an ultrasound coupling and cooling fluid recirculation system; an outlet channel that fluidly couples the outlet port to an input of the ultrasound coupling and cooling fluid recirculation system; and an input channel that fluidly couples an output of the ultrasound coupling and cooling fluid recirculation system to the internal fluid circulation channel. In one or more embodiments, the ultrasound coupling and cooling fluid recirculation system comprises a tank, a pump, a fluid chiller, and a degasser.

BRIEF DESCRIPTION OF THE DRAWINGS

For a fuller understanding of the nature and advantages of the present concepts, reference is made to the detailed description of preferred embodiments in connection with the accompanying drawings.

DETAILED DESCRIPTION

A convertible patient support apparatus includes a patient support bed and a removable patient contact disposed in a hole in the patient support bed. The hole is defined by a support frame. A static membrane is attached to the support frame. A plurality of removable patient contacts can be provided to convert the convertible patient support apparatus based on the patient and/or therapy.

Each patient contact includes an interface frame, a patient contact frame, and a patient contact membrane attached to the patient contact frame. An internal fluid circulation channel is formed between the support frame, the patient contact frame, and the static membrane. The internal fluid circulation channel is configured to circulate ultrasound coupling and cooling fluid in the patient contact.

In one embodiment, the patient contact membrane, the static membrane, and the interface frame form a cavity that is fluidly coupled to the internal fluid circulation channel such that the ultrasound coupling and cooling fluid can flow into and out of the cavity. The patient contact membrane can be rigid such that it maintains it shape when it contacts and receives a force from a patient during use. Alternatively, the patient contact membrane can be deformable such that it deforms in response to contact and force from a patient during use.

In another embodiment, the patient contact membrane is deformable and a raised rigid patient contact is disposed between the deformable patient contact membrane and the static membrane. The raised rigid patient contact can be configured to engage an anatomical structure of a patient during ultrasound therapeutic treatment when the patient is on the patient support bed. A plurality of ultrasound coupling and cooling fluid channels can be defined on or in the raised rigid patient contact.

Figure 1:
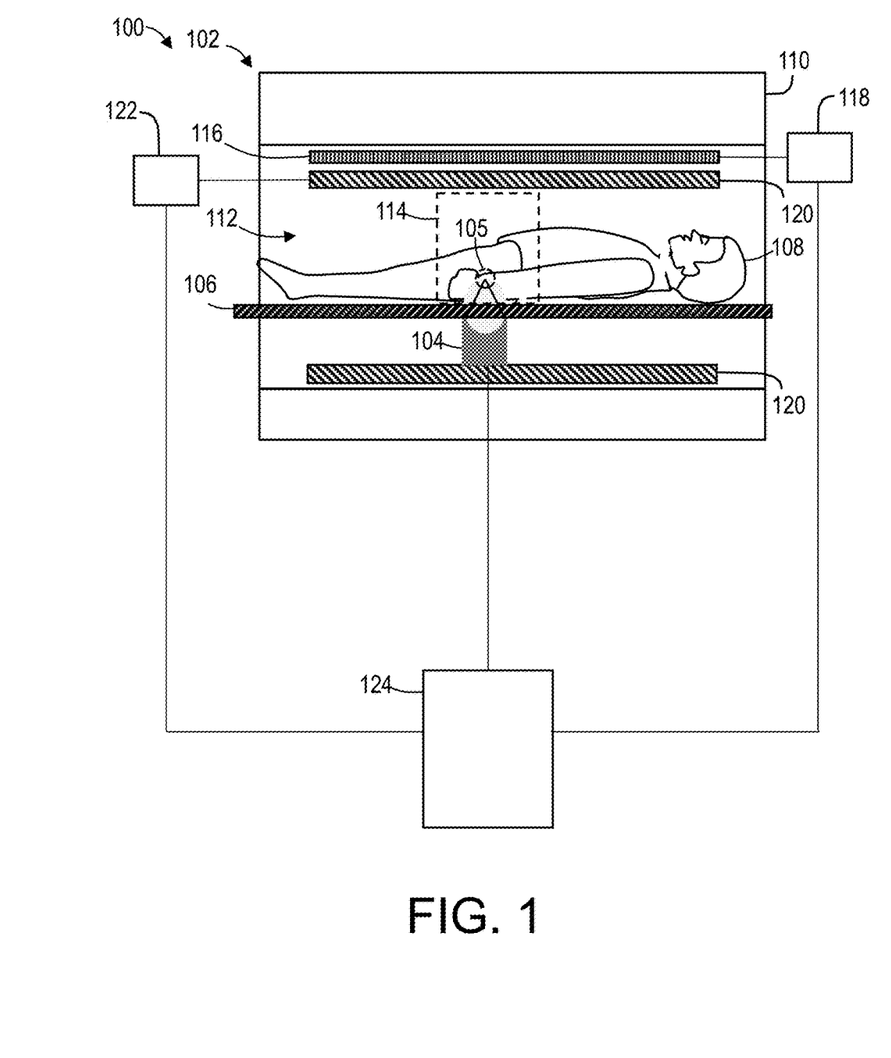
FIG. 1 is a diagram of one type of a medical system in which at least some of the apparatus, systems, and/or methods disclosed herein are employed, in accordance with at least some embodiments.

FIG. 1 is a diagram of one type of a medical system 100 in which at least some of the apparatus, systems, and/or methods disclosed herein are employed, in accordance with at least some embodiments. The system 100 includes a patient support 106 for a patient 108, a magnetic resonance imaging system 102, and an image-guided HIFU system 104.

The magnetic resonance imaging system 102 includes a magnet 110 disposed about an opening 112, an imaging zone 114 in which the magnetic field is strong and uniform enough to perform magnetic resonance imaging, a set of magnetic field gradient coils 116 to change the magnetic field rapidly to enable the spatial coding of MRI signals, a magnetic field gradient coil power supply 118 that supplies current to the magnetic field gradient coils 116 and is controlled as a function of time, a transmit/receive coil 120 (also known as a "body" coil) to manipulate the orientations of magnetic spins within the imaging zone 114, a radio frequency transceiver 122 connected to the transmit/receive coil 120, and a computer 124. The computer 124 includes a hardware-based processor that executes computer-readable instructions (e.g., stored on a non-transitory storage medium operatively coupled to the computer 124) to perform tasks to facilitate operation of the MRI system 102. In addition, the computer 124 is coupled to the radio frequency transceiver 122, the magnetic field gradient coil power supply 118, and the image-guided energy delivery system 104.

The HIFU system 104 includes a therapeutic applicator comprising an array of ultrasonic transducer elements to perform image-guided thermal therapy (e.g., ultrasound therapy) in multiple angular directions to treat a target treatment region. The array of ultrasonic transducer elements are configured and arranged to have a geometric focus 105 that can be electronically steered by adjusting the relative phase of the ultrasound energy generated by each ultrasonic transducer element. The HIFU system 104 is imaged-guided to treat a target treatment region 105 in the patient 108.

The MRI computer 124 can include more than one computer in some embodiments, which can be dedicated for the MRI system 102. In at least some embodiments, the MRI computer 124 and/or one or more other computing devices (not shown) in and/or coupled to the system 100 may also perform one or more tasks (e.g., by executing computer-readable instructions stored on a non-transitory storage medium) to implement one or more aspects and/or embodiments disclosed herein (or portion(s) thereof) to determine the thickness of subcutaneous fat between the therapeutic applicator and the target treatment region and to adjust one or more treatment parameters based on the subcutaneous fat thickness.

One or more of the computers, including computer 124, can include a treatment plan for the patient 108 that includes the target treatment region and the desired or minimal energy (e.g., thermal) dose for the target treatment region. The computer(s) can use images from the magnetic resonance imaging system 102 to image guide the therapeutic applicator (e.g., position and angular orientation). Some or all of the foregoing computers can be in communication with one another (e.g., over a local area network, a wide area network, a cellular network, a WiFi network, or other network), for example through a software-controlled link to a communication network.

Figure 2:
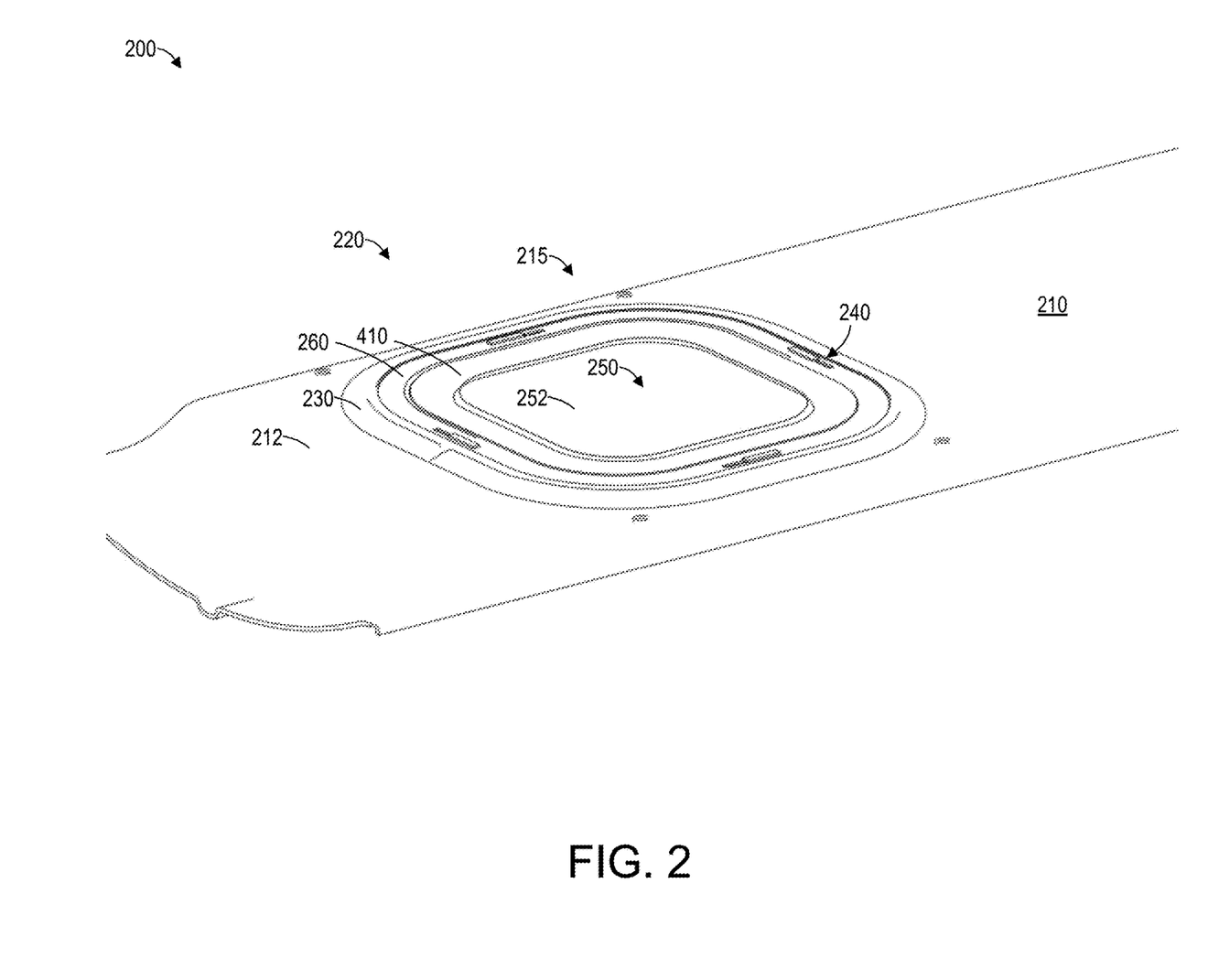
FIG. 2 is a perspective view of a convertible patient support according to an embodiment.

FIG. 2 is a perspective view of a convertible patient support 200 according to an embodiment. The convertible patient support 200 can be the same as patient support 106. The convertible patient support 200 includes a patient support bed 210 and a removable patient contact 220. The removable patient contact 220 is disposed in a hole 215 defined in the patient support bed 210.

A support frame 230 is disposed around or proximal to the perimeter of the hole 215. The support frame 230 is attached to the patient support bed 210. For example, the support frame 230 can be attached to a top surface 212 of the patient support bed 210. The top surface 212 can be a planar surface or a generally planar surface on which a patient (e.g., patient 108) lies during ultrasound therapeutic treatment. Additionally or alternatively, the support frame 230 can be attached to an inner surface of the patient support bed 210 that defines the hole 215. In either case, the support frame 230 can be directly attached to the respective surface or indirectly attached to the respective surface (e.g., the support frame 230 can be attached to an underlying structure that is directly attached to the surface).

The removable patient contact 220 includes optional mechanical locks 240, a patient contact membrane 250, the interface frame 260, and a patient contact frame 410.

The mechanical locks 240 (e.g., a mechanical locking mechanism) releasably attach the removable patient contact 220 to the support frame 230. The mechanical locks 240 include a slideable structure that can slide in a first direction to engage a complementary structure in the underlying support frame 230 to secure the removable patient contact 220 relative to the support frame 230. The slideable structure can slide in a second direction, opposite to the first direction, to disengage the complementary structure in the underlying support frame 230 to unlock the removable patient contact 220 from the support frame 230. The slideable structure can include a rod, a projection, a fin, or other structure. The complementary structure can include a groove, recess, or other complementary structure. Alternatively, the mechanical locks 240 can include a rotatable structure (e.g., as in a window sash lock), a latch, or other structure. Or the top frame structure could accommodate a rotational lock mechanism such as bayonet lock or threaded lid.

The patient contact membrane 250 is attached to (e.g., fixedly attached to) the patient contact frame 410. The patient contact membrane 250 contacts the patient's skin proximal to the target treatment region during ultrasound therapeutic treatment. The patient contact membrane 250 encloses and contains the ultrasound coupling and cooling fluid that circulates in the removable patient contact 220 below. The membrane is constructed in such a way that it can transmit ultrasound from an ultrasound device (e.g. image-guided HIFU system 104) to the patient, and also conduct heat energy away from the patient.

The patient contact membrane 250 can be rigid or deformable. When the patient contact membrane 250 is rigid, the patient contact membrane 250 (e.g., the exposed patient contact surface 252 of the patient contact membrane 250) maintains a predetermined shape when the patient applies a force thereto, such as by laying on the patient support bed 210 or placing a limb on the removable patient contact 220. The predetermined shape of the patient contact membrane 250 can be planar (e.g., as illustrated in FIG. 2) or non-planar. Examples of non-planar patient contact membrane surfaces includes one or more raised planar regions (e.g., plateaus) that can be configured to engage an anatomical feature in the patient during ultrasound therapeutic treatment. The rigid patient contact membrane 250 can comprise an ultrasound gel pad.

When the patient contact membrane 250 is deformable, the patient contact membrane 250 (e.g., the exposed patient contact surface 252 of the patient contact membrane 250) deforms when the patient applies a force thereto, such as by laying on the patient support bed 210 or placing a limb on the removable patient contact 220. For example, the patient contact membrane can conform, partially or fully, to the patient's body (e.g., similar to a water bed). The deformable patient contact membrane can comprise a thermoplastic elastomer (TPE).

Figure 3:
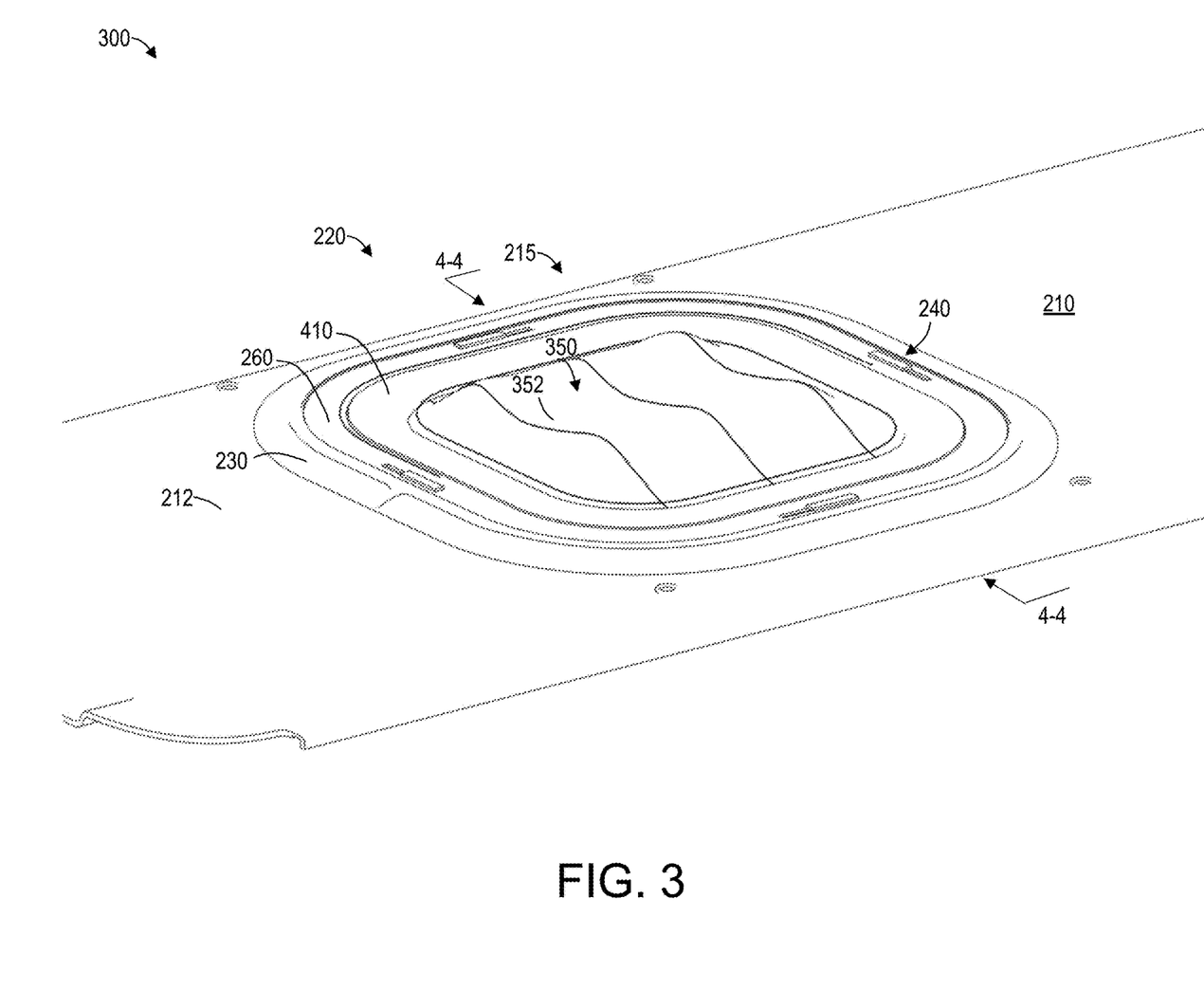
FIG. 3 is a perspective view of a convertible patient support according to an embodiment.

FIG. 3 is a perspective view of a convertible patient support 300 according to an embodiment. Convertible patient support 300 is identical to convertible patient support 200 except that the removable patient contact 220 in convertible patient support 300 includes a deformable patient contact membrane 350 instead of the patient contact membrane 250.

Figure 4:
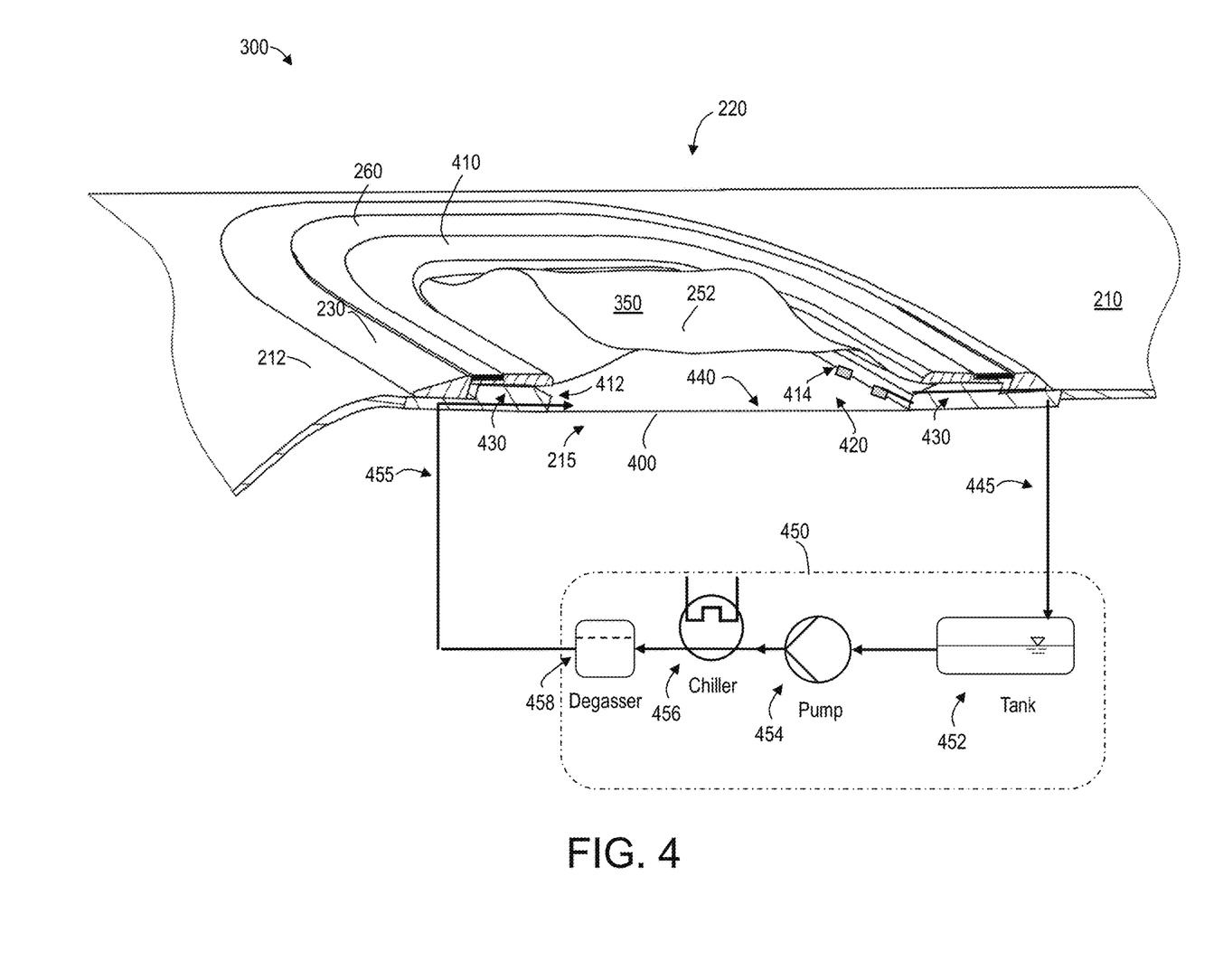
FIG. 4 is a cross section of the convertible patient support illustrated in FIG. 3.

FIG. 4 is a cross-sectional view of convertible patient support 300 through line 4-4 in FIG. 3. The cross-section view of convertible patient support 300 is representative of the cross-section view of convertible patient support 200 except that the removable patient contact 220 in convertible patient support 300 includes a deformable patient contact membrane 350 instead of the patient contact membrane 250.

The cross-sectional view illustrates that the convertible patient support 300 includes a static or fixed membrane 400 (in general, static membrane 400) and a patient contact frame 410. The static membrane 400 can comprise BoPET (biaxially-oriented polyethylene terephthalate) (e.g., MYLAR® available from DuPont Teijin Films). The static membrane 400 is attached (e.g., fixedly attached) to the support frame 230, which is attached (e.g., fixedly attached) to the patient support bed 210. The removable patient contact 220 includes the interface frame 260, the patient contact frame 410, and the deformable patient contact membrane 350. The interface frame 260 is attached (e.g., fixedly attached) to the patient contact frame 410, which is attached (e.g., fixedly attached) to the deformable patient contact membrane 350. Optional mechanical locks 240 on the interface frame 260 can releasably secure the interface frame 260 (and thus the removably patient contact 220) to the support frame 230. Thus, the patient contact frame 410 is indirectly attached to the support frame 230.

In some embodiments, the interface frame 260 is optional in which case the patient contact frame 410 is removably attached to the support frame 230.

A cavity 420 is formed between the deformable patient contact membrane 350, the static membrane 400, and the interface frame 260. The cavity 420 is in fluid communication with one or a plurality of inlet port(s) 412 in the cavity 420 to receive an ultrasound coupling and cooling fluid (e.g., water) from an internal fluid circulation channel 430. In some embodiments, the internal fluid circulation channel 430 and the optional plurality of inlet ports 412 can function as a manifold. The internal fluid circulation channel 430 is formed between the support frame 230, the patient contact frame 410, and the static membrane 400. The patient contact frame 410 can include gaskets to provide a fluid-tight seal for the internal fluid circulation channel 430. The weight of the convertible patient support 300 and the patient laying thereon can improve the fluid-tight seal caused by the gaskets.

The ultrasound coupling and cooling fluid can exit the cavity 420 via one or more outlet port(s) 414 in the cavity 420. The outlet port(s) 414 are fluidly coupled to an outlet channel 445 to direct the ultrasound coupling and cooling fluid to an ultrasound coupling and cooling fluid recirculation system 450. Alternatively, in some embodiments the cavity 420 can include a single port for introducing and/or receiving the ultrasound coupling and cooling fluid.

The ultrasound coupling and cooling fluid recirculation system 450 includes a tank 452, a pump 454, a chiller or heat exchanger 456 (e.g., to regulate or control the temperature of the ultrasound coupling and cooling fluid which is heated during circulation), and a degasser 458. The ultrasound coupling and cooling fluid flows out of the cavity 420 via the outlet ports 414 and an outlet channel 445 into the tank 452 to transfer heat away from the cavity 420 and the patient's skin. A pump 454 feeds the heated ultrasound coupling and cooling fluid from the tank 452 into a chiller unit 456 and a degasser 458 where the ultrasound coupling and cooling fluid is cooled and cleared of air bubbles, respectively. After passing through the ultrasound coupling and cooling fluid recirculation system 450, the temperature-controlled ultrasound coupling and cooling fluid is recirculated to the internal fluid circulation channel 430 through an input channel 455.

When the ultrasound coupling and cooling fluid fills the cavity 420, the deformable patient contact membrane 350 (e.g., including exposed patient contact surface 352) is displaced away from the static membrane 400. When the ultrasound coupling and cooling fluid is removed from the cavity 420, the deformable patient contact membrane 350 (e.g., including exposed patient contact surface 352) can deform or bend towards the static membrane 400.

The static membrane 400 can have a generally planar surface that faces the cavity 420. The static membrane 400 can be attached to the support frame 230 using an adhesive or another attachment means. A fluid-tight seal (or a substantially fluid-tight seal) can be formed by the attachment between the static membrane 400 and the support frame 230.

During treatment, an ultrasound applicator (e.g., in image-guided HIFU system 104) is placed below the hole 215 defined in the patient support bed 210. Ultrasound energy passes through the static membrane 400, the ultrasound coupling and cooling fluid, and the deformable patient contact membrane 350 and into the patient where the ultrasound energy is focused on a target volume. The path of the ultrasound energy does not include any structures that are opaque to ultrasound energy transmission.

In addition to providing a path for ultrasound energy to travel, the ultrasound coupling and cooling fluid regulates the temperature of the patient's skin which is heated during treatment. Only a small fraction of the ultrasound energy is conducted through the skin to the target volume. The remaining ultrasound energy is absorbed by the skin tissue, resulting in heating of the skin. This occurs due to density differences in the boundary layer between the skin and the deformable patient contact membrane 350. The energy-conduction ratio decreases significantly if air, which was a much lower density, is able to flow into any gaps in the boundary layer. Therefore, a good skin-membrane boundary layer is desired for a high energy-conduction ratio and to prevent skin burns.

Figure 5:
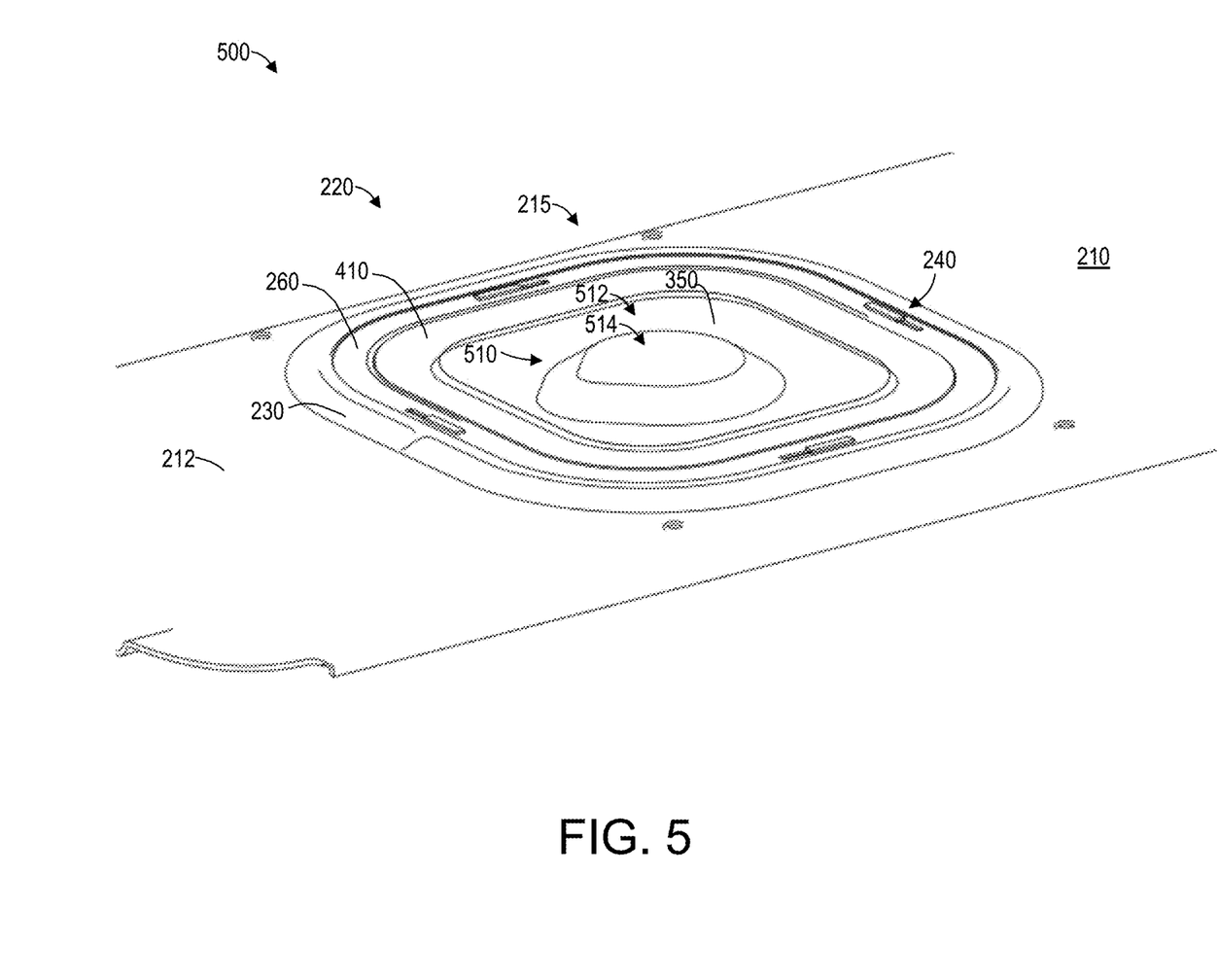
FIG. 5 is a perspective view of a convertible patient support according to an embodiment.

FIG. 5 is a perspective view of a convertible patient support 500 according to an embodiment. Convertible patient support 500 is identical to convertible patient support 300 except that the removable patient contact 220 in convertible patient support 500 includes a raised rigid patient contact structure 510 disposed between the deformable patient contact membrane 350 and the static membrane 400. The raised rigid patient contact structure 510 is attached to the patient contact frame 410.

The raised rigid patient contact structure 510 has a height that is measured with respect an axis that is orthogonal to the plane defined by a planar portion 512 of the raised rigid patient contact structure 510. The top 514 of the raised rigid patient contact structure 510 is generally planar such that the raised rigid patient contact structure 510 forms a plateau. The illustrated plateau is in a teardrop shape. In other embodiments, the plateau can have a heart shape, a round shape (e.g., circle, oval, or other round shape), a rectangular shape, or another shape. Alternatively, the raised rigid contact structure 510 can be in the form of a dome. Additionally or alternatively, the raised rigid contact structure 510 can be in a form other than a plateau or a dome, or it can include multiple (e.g., 2 or more) raised structures.

The teardrop shape illustrated in FIG. 5 is configured to displace certain patient organs (e.g., stomach and/or liver), not intended for therapy, out of the path of the ultrasound beam when providing therapeutic ultrasound therapy to the target organ (e.g., pancreas). In addition to displacing sensitive organs, the raised rigid patient contact structure 510 functions as an ultrasonic coupling medium through which therapeutic ultrasound energy can be transmitted from an ultrasound device (e.g., image-guided HIFU system 104) to the patient.

The deformable patient contact membrane 350 is disposed over the raised rigid patient contact structure 510 and generally conforms to the shape thereof. For example, in FIG. 5 the deformable patient contact membrane 350 generally conforms to the teardrop shape of the raised rigid patient contact structure 510.

Figure 6:
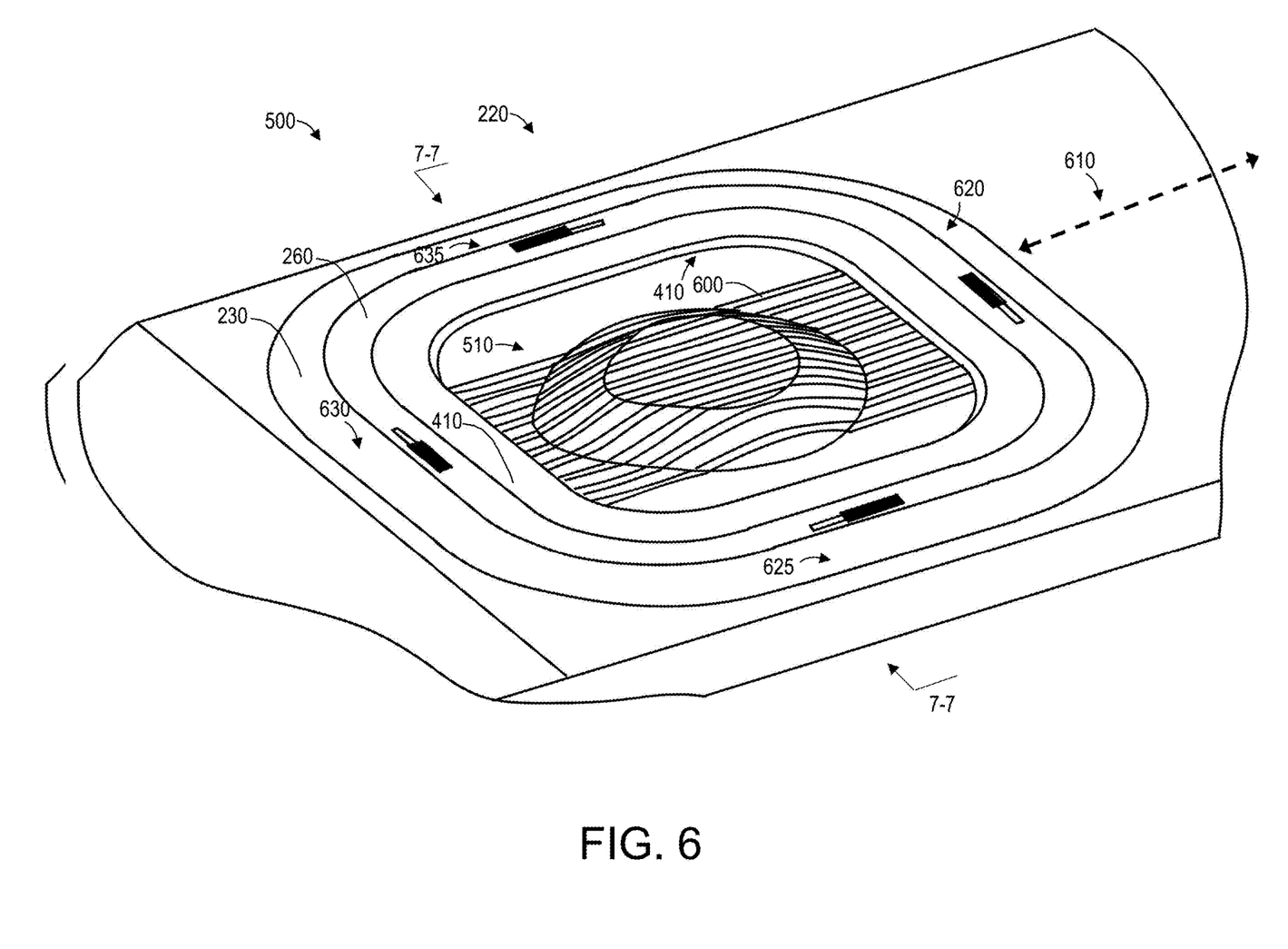
FIG. 6 is a perspective view of the convertible patient support to illustrate a first embodiment of cooling channels on the raised rigid patient contact illustrated in FIG. 5.

FIG. 6 is a perspective view of the convertible patient support 500 to illustrate a first embodiment of cooling channels 600 on the raised rigid patient contact structure 510. The cooling channels 600 extend parallel to each other across opposing sides 620, 630 of the patient contact frame 410. The cooling channels 600 also extend parallel to a central axis 610 of the convertible patient support 500 (e.g., that extends from a head support to a foot support of the convertible patient support 500).

Each cooling channel 600 is preferably fluidly coupled to a respective inlet port on one side of the support frame 230 (e.g., to receive the ultrasound coupling and cooling fluid such as water) and to a respective outlet port on the opposing side of the support frame 230 (e.g., to output the ultrasound coupling and cooling fluid such as water). For example, each cooling channel 600 can be fluidly coupled to a respective inlet port on a first side 620 of the support frame 230 and to a respective outlet port on a second side 630 of the support frame 230. Alternatively, each cooling channel 600 can be fluidly coupled to a respective inlet port on the second side 630 of the support frame 230 and to a respective outlet port on the first side 620 of the support frame 230. The inlet and outlet ports are fluidly coupled to the internal fluid circulation channel 430.

In an alternative embodiment, the cooling channels 600 can extend parallel to each other across opposing sides 625, 635 of the patient contact frame 410 and orthogonal to the central axis 610. The cooling channels 600 can be fluidly coupled to respective inlet ports on a third side 625 of the support frame 230 and to respective outlet ports on a fourth side 635 of the support frame 230. Alternatively, the cooling channels 600 can be fluidly coupled to respective inlet ports on the fourth side 635 of the support frame 230 and to respective outlet ports on the third side 425 of the support frame 230.

Figure 7:
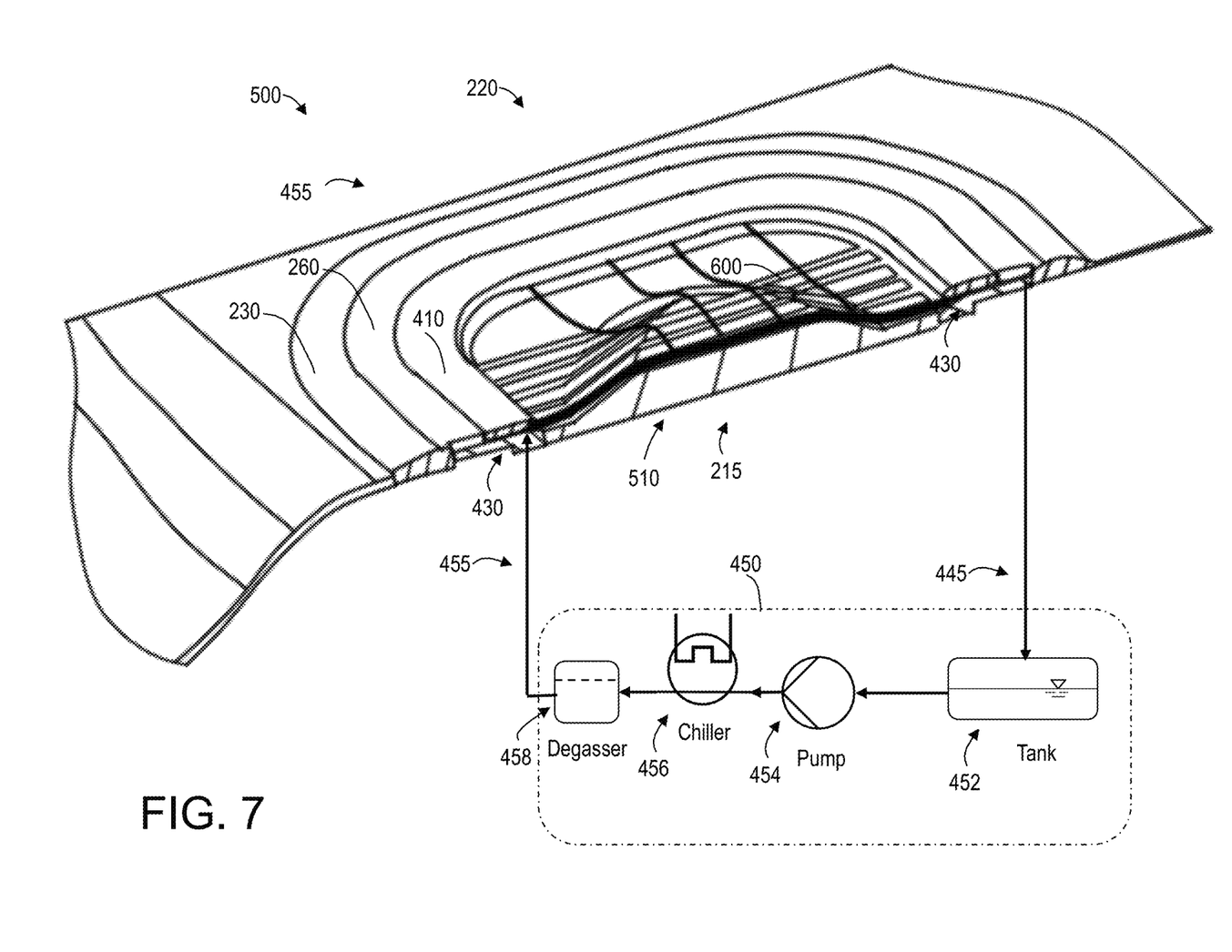
FIG. 7 is a cross section of the convertible patient support illustrated in FIG. 6.

FIG. 7 is a cross-sectional view of convertible patient support 500 through line 7-7 in FIG. 6. For clarity, the deformable patient contact membrane 350 is not illustrated in FIG. 7. The convertible patient support 500 is fluidly coupled to an ultrasound coupling and cooling fluid recirculation system 450. The ultrasound coupling and cooling fluid flows out of the raised rigid patient contact structure 510 via the outlet ports 414 and outlet channel 445 into the tank 452 to transfer heat away from the raised rigid patient contact structure 510. A pump 454 feeds the heated ultrasound coupling and cooling fluid from the tank 452 into a chiller unit 456 and a degasser 458 that cool the ultrasound coupling and cooling fluid and remove dissolved gasses from it (e.g., which may form bubbles in the ultrasound coupling and cooling fluid when exposed to negative pressure waves in the ultrasound beam), respectively The ultrasound coupling and cooling fluid is fed via the inlet channel 455 into the internal fluid circulation channel 430. Thus, the ultrasound coupling and cooling fluid can flow from a tank or reservoir 452, through one or more inlet channels 455 to the internal fluid circulation channel 430 (via pump 454), to the inlet ports, then through the cooling channels 600, and out through the outlet ports in the internal fluid circulation channel 430, and back to the tank or reservoir 452 via one or more outlet channels 445.

During treatment, an ultrasound applicator (e.g., in image-guided HIFU system 104) is placed below the hole 215 defined in the patient support bed 210. Ultrasound energy passes through the static membrane 400, the ultrasound coupling and cooling fluid, the raised rigid patient contact structure 510, and the deformable patient contact membrane 350 and into the patient where the ultrasound energy is focused on a target volume. The path of the ultrasound energy does not include any structures that are opaque to ultrasound energy transmission.

Figure 8:
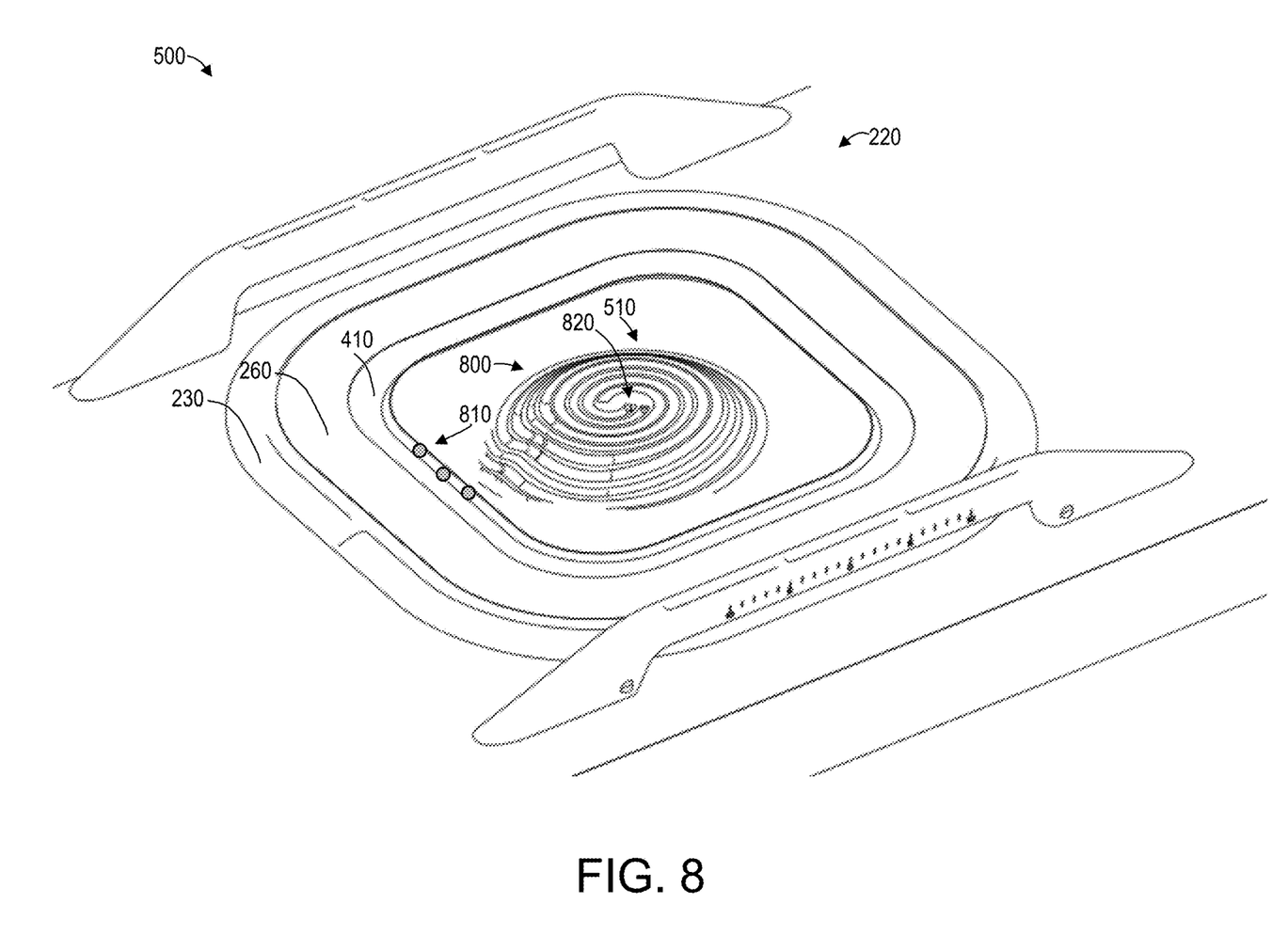
FIG. 8 is a perspective view of convertible patient support to illustrate a second embodiment of cooling channels on the raised rigid patient contact structure illustrated in FIG. 5.

FIG. 8 is a perspective view of convertible patient support 500 to illustrate a second embodiment of cooling channels 800 on or in the raised rigid patient contact structure 510. For clarity, the deformable patient contact membrane 350 is not illustrated in FIG. 8. The cooling channels 800 extend in a spiral around the raised rigid patient contact structure 510. The illustrated spiral is formed of three cooling channels 800. Additional or fewer cooling channels 800 can form the spiral in other embodiments.

The cooling channels 800 can be fluidly coupled to one or more inlet ports 810 in the internal fluid circulation channel 430 (e.g., to receive the ultrasound coupling and cooling fluid). An output hole or channel 820 can be formed through the spiral (e.g., through the center of the spiral) to receive the ultrasound coupling and cooling fluid from the termination of the cooling channels 800. The hole or channel 820 can be fluidly coupled to the tank 452 of the ultrasound coupling and cooling fluid recirculation system 450, such as through outlet channel 445. One or more inlet channels (e.g., inlet channels 455) can fluidly couple the output of the ultrasound coupling and cooling fluid recirculation system 450 to the internal fluid circulation channel 430.

It is recognized that the cooling channels 600, 800 can have other fluid paths and/or configurations. The paths and configurations 600, 800 are provided as non-limiting examples only.

Figure 9:
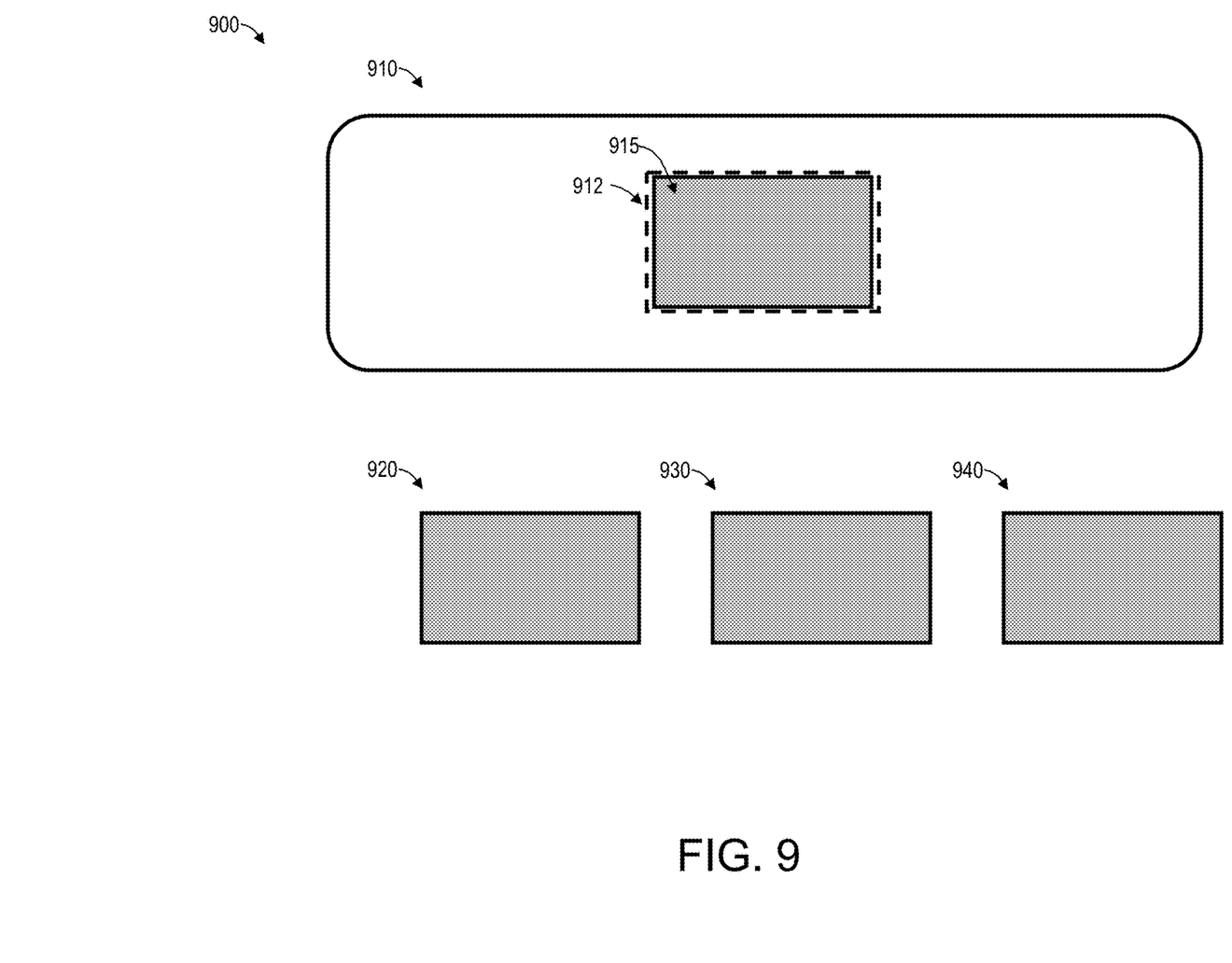
FIG. 9 is a block diagram of a kit according to an embodiment.

FIG. 9 is a block diagram of a kit 900 according to an embodiment. The kit 900 includes a convertible patient support 910 and removable patient contacts 920, 930, 940. The convertible patient support 910 can be the same as any of the convertible patient supports described herein (e.g., convertible patient support 200, convertible patient support 300, or convertible patient support 500). The convertible patient support 910 can include a removable patient contact 915 (e.g., removable patient contact 220) or the removable patient contact 915 can be removed. In either case, the convertible patient support 910 is configured to releasably receive one of a plurality of removable patient contacts 920, 930, 940 in a hole 912 defined in the convertible patient support 910.

Each removable patient contact 920, 930, 940 can be configured the same or different than the others. For example, removable patient contact 920 can be the same as described above with respect to FIG. 2 (e.g., having a patient contact membrane 250). Removable patient contact 930 can be the same as described above with respect to FIGS. 3 and 4 (e.g., having a deformable patient contact membrane 350). Removable patient contact 930 can be the same as described above with respect to any of FIGS. 5-8 (e.g., having a raised rigid patient contact structure 510)

The invention should not be considered limited to the particular embodiments described above, but rather should be understood to cover all aspects of the invention as fairly set out in the attached claims. Various modifications, equivalent processes, as well as numerous structures to which the invention may be applicable, will be apparent to those skilled in the art to which the invention is directed upon review of this disclosure. The claims are intended to cover such modifications and equivalents.

What is claimed is:

1. A convertible patient support apparatus comprising:
   a patient support bed having a hole defined therein;
   a support frame disposed on or in the hole, the support frame attached to the patient support bed; and
   a static membrane fixedly attached to the support frame; and
   a removable patient contact including:
      an interface frame removably attached to the support frame;
      a patient contact frame fixedly attached to the interface frame; and
      a patient contact membrane fixedly attached to the interface frame,
   wherein:
      the patient contact membrane, the static membrane, and the interface frame define a cavity, the cavity having a port to introduce or remove an ultrasound coupling and cooling fluid to or from the cavity.

2. The apparatus of claim 1, wherein the static membrane is disposed below the removable patient contact.

3. The apparatus of claim 2, wherein the static membrane is rigid.

4. The apparatus of claim 2, wherein the patient contact membrane is deformable.

5. The apparatus of claim 1, wherein:
   the port comprises an inlet port,
   an internal fluid circulation channel is formed between the patient contact frame, the static membrane, and the support frame, and
   the internal fluid circulation channel provides the ultrasound coupling and cooling fluid to the cavity through the inlet port and receives the ultrasound coupling and cooling fluid from the cavity through the outlet port.

6. The apparatus of claim 5, further comprising:
an ultrasound coupling and cooling fluid recirculation system;
an outlet channel that fluidly couples the outlet port to an input of the ultrasound coupling and cooling fluid recirculation system; and
an input channel that fluidly couples an output of the ultrasound coupling and cooling fluid recirculation system to the internal fluid circulation channel.

7. The apparatus of claim 6, wherein the ultrasound coupling and cooling fluid recirculation system comprises a tank, a pump, a fluid chiller, and a degasser.

8. The apparatus of claim 1, further comprising mechanical locks that releasably securely attach the interface frame to the support frame.

9. A convertible patient support apparatus comprising:
a patient support bed having a hole defined therein;
a support frame disposed on or in the hole, the support frame attached to the patient support bed; and
a static membrane fixedly attached to the support frame; and
a removable patient contact comprising:
an interface frame removably attached to the support frame;
a patient contact frame fixedly attached to the interface frame;
a patient contact membrane fixedly attached to the interface frame;
a raised rigid patient contact attached to the patient contact frame, the raised rigid patient contact disposed between the patient contact membrane and the static membrane; and
a plurality of circulation channels disposed on or in the raised rigid patient contact,
wherein:
an internal fluid circulation channel is formed between the patient contact frame, the static membrane, and the support frame,
the circulation channels are fluidly coupled to one or more inlet ports in the internal fluid circulation channel to receive the ultrasound coupling and cooling fluid, and
the circulation channels are fluidly coupled to one or more outlet ports in the internal fluid circulation channel to output the ultrasound coupling and cooling fluid.

10. The apparatus of claim 9, wherein the raised rigid patient contact is configured to engage an anatomical structure of a patient during an ultrasound therapeutic treatment when the patient is on the patient support bed.

11. The apparatus of claim 9, wherein the circulation channels extend parallel to each other.

12. The apparatus of claim 9, wherein the circulation channels form a spiral.

13. The apparatus of claim 12, wherein an output channel is formed through the spiral to receive the ultrasound coupling and cooling fluid from a termination of the circulation channels.

14. The apparatus of claim 13, wherein the output channel is fluidly coupled to the one or more outlet ports in the internal fluid circulation channel.

15. The apparatus of claim 13, wherein the output channel is fluidly coupled to an ultrasound coupling and cooling fluid recirculation system.

16. The apparatus of claim 15, wherein the ultrasound coupling and cooling fluid recirculation system comprises a tank, a pump, a fluid chiller, and a degasser.

17. The apparatus of claim 9, further comprising mechanical locks that releasably securely attach the interface frame to the support frame.

18. A kit comprising
a convertible patient apparatus comprising:
a patient support bed having a hole defined therein;
a support frame disposed on or in the hole, the support frame attached to the patient support bed; and
a static membrane fixedly attached to the support frame; and
a plurality of removable patient contacts, each removable patient contact including:
an interface frame configured to be removably attached to the support frame;
a patient contact frame fixedly attached to the interface frame; and
a patient contact membrane fixedly attached to the patient contact frame,
wherein when the interface frame of one of the removable patient contacts is attached to the support frame to form an attached patient contact, an internal fluid circulation channel is formed between the patient contact frame of the attached patient contact, the static membrane, and the support frame.

19. The kit of claim 18, wherein:
the plurality of removable patient contacts includes a first removable patient contact, and
when the first removable patient contact is attached to the support frame, the patient contact membrane and the static membrane define a cavity having a port that is fluidly coupled to the internal fluid circulation channel to introduce or remove an ultrasound coupling and cooling fluid to or from the cavity.

20. The kit of claim 19, wherein:
when the first removable patient contact is attached to the support frame:
the port comprises an inlet port,
the cavity has an outlet port that is fluidly coupled to the internal fluid circulation channel, and
the cavity receives the ultrasound coupling and cooling fluid from the inlet port and outputs the ultrasound coupling and cooling fluid through the outlet port.

21. The kit of claim 20, wherein the internal fluid circulation channel is fluidly coupled to an ultrasound coupling and cooling fluid recirculation system.

22. The kit of claim 21, wherein the ultrasound coupling and cooling fluid recirculation system comprises a tank, a pump, a fluid chiller, and a degasser.

23. The kit of claim 19, wherein when the first removable patient contact is attached to the support frame, the static membrane is disposed below the first removable patient contact.

24. The kit of claim 19, wherein the patient contact membrane of the first removable patient contact is deformable.

25. The kit of claim 19, wherein:
the plurality of removable patient contacts includes a second removable patient contact; and
in the second removable patient contact:
a raised rigid patient contact is attached to the patient contact frame;
a plurality of circulation channels are disposed on or in the raised rigid patient contact, the circulation channels configured to receive the ultrasound coupling and cooling fluid from one or more inlet ports in the internal fluid circulation channel to output the ultrasound coupling and cooling fluid to one or more outlet ports in the internal fluid circulation channel; and when the second removable patient contact is attached to the support frame, the raised rigid patient contact of the second removable patient contact is disposed between the patient contact membrane and the static membrane.

26. The kit of claim 25, wherein the raised rigid patient contact is configured to engage an anatomical structure of a patient during an ultrasound therapeutic treatment when:
the patient is on the patient support bed, and
the second removable patient contact is attached to the support frame.

27. The kit of claim 25, wherein the circulation channels, disposed on or in the raised rigid patient contact, extend parallel to each other.

28. The kit of claim 25, wherein the circulation channels, disposed on or in the raised rigid patient contact, form a spiral.

29. The kit of claim 28, wherein an output channel is formed through the spiral to receive the ultrasound coupling and cooling fluid from a termination of the circulation channels.

30. The kit of claim 29, wherein the output channel is fluidly coupled to the one or more outlet ports in the internal fluid circulation channel.

31. The kit of claim 29, wherein the output channel is fluidly coupled to an ultrasound coupling and cooling fluid recirculation system.

32. The kit of claim 31, wherein the ultrasound coupling and cooling fluid recirculation system comprises a tank, a pump, a fluid chiller, and a degasser.

33. The kit of claim 25, wherein:
the plurality of removable patient contacts includes a third removable patient contact, and
in the third removable patient contact:
the patient contact membrane is rigid;
the patient contact membrane, the static membrane, and the interface frame define a cavity having an inlet port and an outlet port that are fluidly coupled to the internal fluid circulation channel; and
the cavity receives the ultrasound coupling and cooling fluid from the inlet port in the circulation frame and outputs the ultrasound coupling and cooling fluid through the outlet port.

34. The kit of claim 18, further comprising mechanical locks that releasably securely attach the interface frame of each removable patient contact to the support frame.

35. The kit of claim 18, wherein the static membrane is rigid.

36. A system comprising:
a convertible patient support comprising:
a patient support bed having a hole defined therein;
a support frame disposed on or in the hole, the support frame attached to the patient support bed;
a static membrane fixedly attached to the support frame; and
a removable patient contact including:
an interface frame removably attached to the support frame;
a patient contact frame fixedly attached to the interface frame; and
a patient contact membrane fixedly attached to the interface frame,
wherein:
the patient contact membrane, the static membrane, and the interface frame define a cavity, the cavity having a port to introduce or remove an ultrasound coupling and cooling fluid to or from the cavity, and
a high intensity focused ultrasound (HIFU) system for sonicating a sonication volume of a patient, the HIFU system including an ultrasound applicator disposed below the hole in the patient support bed, the ultrasound applicator generating ultrasound energy having a path through the static membrane, the ultrasound coupling and cooling fluid, and the patient contact membrane to reach a target volume in the patient.

37. The system of claim 36, wherein the path of the ultrasound energy does not include any structures that are opaque to ultrasound energy transmission.

38. The system of claim 36, wherein:
the port comprises an inlet port,
an internal fluid circulation channel is formed between the patient contact frame, the static membrane, and the support frame, and
the internal fluid circulation channel provides the ultrasound coupling and cooling fluid to the cavity through the inlet port and receives the ultrasound coupling and cooling fluid from the cavity through the outlet port.

39. The system of claim 38, wherein an internal fluid circulation channel is formed between the patient contact frame, the static membrane, and the support frame, the internal fluid circulation channel providing the ultrasound coupling and cooling fluid to the cavity through the inlet port and receiving the ultrasound coupling and cooling fluid from the cavity through the outlet port.

40. The system of claim 39, further comprising:
an ultrasound coupling and cooling fluid recirculation system;
an outlet channel that fluidly couples the outlet port to an input of the ultrasound coupling and cooling fluid recirculation system; and
an input channel that fluidly couples an output of the ultrasound coupling and cooling fluid recirculation system to the internal fluid circulation channel.

41. The system of claim 40, wherein the ultrasound coupling and cooling fluid recirculation system comprises a tank, a pump, a fluid chiller, and a degasser.

* * * * *